United States Patent [19]

Rosenstein et al.

[11] Patent Number: 4,618,576

[45] Date of Patent: Oct. 21, 1986

[54] DIAGNOSTIC TEST FOR STREPTOCOCCUS A

[75] Inventors: Robert Rosenstein, Ellicott City; Kim P. Aspden, Reisterstown; Peter Stopa, Timonium, all of Md.

[73] Assignee: Becton Dickinson and Company, Franklin Lakes, N.J.

[21] Appl. No.: 584,175

[22] Filed: Feb. 27, 1984

[51] Int. Cl.$^4$ .................. G01N 33/53; C12Q 1/04; C12M 1/40; C12M 1/30

[52] U.S. Cl. .......................................... 435/7; 435/34; 435/36; 435/39; 435/288; 435/291; 435/295

[58] Field of Search .............. 435/7, 34, 39, 36, 810, 435/288, 295, 291; 436/533, 530, 534, 528, 810, 808

[56] References Cited

U.S. PATENT DOCUMENTS 4,203,724  5/1980  Sawai et al. ..................... 23/230 B
4,497,900  2/1985  Abram et al. ..................... 436/511
4,525,452  6/1985  Jones et al. ..................... 435/7

OTHER PUBLICATIONS

E. M. Barnes et al, Streptocci, "Isolation Media for Streptococci", Academic Press, Skinner & Quesnell, pp. 371-378, 1978.

"Method in Microbiology", (ASM), Section 8.2.9, p. 121.

"Culturing Techniques", CRC Critical Reviews in Clinical Laboratory Sciences, pp. 291-299, Mar. 1976.

F. O. Pien et al, Health Lab Science, vol. 15, pp. 189-191, 1978.

Gunn et al, Journal of Clinical Microbiology, vol. 5, No. 6, 650-655, 1977.

von Graevenitz, Clinical Microbiology Newsletter, vol. 5, No. 14, 94-95, 1981.

Vincent et al, Applied Microbiology, vol. 22, No. 5, 942-943, 1971.

Blanchette et al, The American Journal of Clinical Pathology, vol. 48, No. 4, 441-443, 1967.

Lawbury et al, J of Clinical Pathology, vol. 17, 231-235, 1964.

Dykstra et al, J of Clinical Microbiology, vol. 9, No. 2, 236-238, 1979.

Primary Examiner—Sidney Marantz
Assistant Examiner—Patricia DeSantis
Attorney, Agent, or Firm—James R. McBride

[57] ABSTRACT

The presence of Group A Streptococcus in a biological specimen is determined from the presence of Streptococcus A antigen. A biological specimen is collected with an applicator having a plastic stick with a rayon swab. The swab is placed in an extraction reagent containing enzymes produced by the bacterium *Streptomyces albus*, wherein the enzymes release the antigen from the fiber. An aliquot of the extraction medium is mixed with an indicator reagent containing an antibody reactive with the antigen. The occurrence or non-occurrence of an antibody-antigen reaction is noted which indicates the presence or absence of Group A Streptococcus in the biological specimen.

12 Claims, No Drawings

DIAGNOSTIC TEST FOR STREPTOCOCCUS A

The present invention relates to the detection of infectious agents through an antibody-antigen reaction and more particularly to the detection of Streptococcus A through the presence in a biological sample of Streptococcus A antigen.

BACKGROUND OF THE INVENTION

Of the several groups of Streptococci, group A streptococcus (*S. pyogenes*) is primarily responsible for causing pathological conditions in humans, such as B-hemolytic pneumonia, scarlet fever, rheumatic fever, cardiac sequelae, glomerulonephritis, septic sore throat, and puerperal sepsis. Other groups of Streptococci are wholly innocuous and normally exist, for example, in the throat. Because of the serious nature of infections potentially caused by Streptococcus A, it is important to diagnose its presence in an early stage of infection so that an appropriate course of treatment may be selected. Streptococci may be cultured conventionally in suitable media; however, identifying Streptococci by type is not a simple task. Streptococci A-selective culture media are less than perfect in that they are not fully selective, i.e., they do not eliminate all other types of Streptococci while allowing Streptococcus A to grow. Importantly, culturing techniques for identifying Streptococci A generally require an incubation time of 18 hours, and frequently as long as 48 hours, to ascertain the presence of Streptococcus A. Such lengthy tests delay a fully informed judgment as to the best course of disease treatment. The desirability of a reliable, simple and quick test for Streptococcus A is clearly indicated.

SUMMARY OF THE INVENTION

Testing for the presence of Streptococcus A in a biological sample, such as a saliva sample from the throat, is quick and reliable using a test kit provided by the present invention. An applicator, including a stick and a Streptococcus A antigen collecting-fiber swab at one end, is used to swab an infected area. After a sample is taken with the swab, the swab is dipped in an extraction reagent that releases the antigen from the swab fibers into the reagent. An aliquot of the extraction reagent is introduced into an indicator solution that contains an antibody reactive to the antigen. Occurrence or non-occurrence of an antibody-antigen reaction is indicative of the presence or absence of Streptococcus A in the biological sample.

Several features of the invention have been found to promote reliable results. Regenerated cellulose fiber, commonly known as rayon, is most effective for collecting and releasing (in the presence of enzymes) Streptococcus A antigen, whereas natural cellulosic fibers, e.g. cotton, do not work well. It is preferable that the stick be formed of a non-porous material, most preferably a synthetic, non-porous material such as a non-porous plastic rather than a natural material, such as wood. The preferred extraction reagent contains an enzyme mixture produced by the bacterium *Streptomyces albus*. The preferred indicator reagent is an agglutination reagent in which antibody that is reactive with the Streptococcus A antigen is bound to latex particles so that the particles agglutinate as a result of an antigen-antibody reaction.

DETAILED DESCRIPTION OF THE PREFERRED EMBODIMENT

Provided herein is a diagnostic test for group A Streptococcus which can be performed in a very short time, i.e., less than about 70 minutes, and without the use of complicated equipment. This permits the test to be performed in a doctor's office and enables the doctor to determine a course of treatment based upon the results of the test the same day. The test detects the presence of Streptococcus A antigen in a biological sample, such as a swab specimen from the throat, rather than growth of the Streptococcus A organism itself, as is done in culture tests. Hence, the extended incubation period required for selective culturing tests is substantially eliminated. The advantages of the invention; however, are not obtained at the expense of either sensitivity or accuracy as studies have shown that both sensitivity and accuracy of the assay of the invention test approach 100%.

In accordance with the invention, a test kit provides the materials and reagents by which the presence of Streptococcus A antigen in a biological specimen is accurately detected. A specimen is collected by means of an applicator that includes an applicator stick and a fiber swab at one end of the stick. The area of infection is swabbed with the fiber swab, whereby Streptococcus A antigen is collected by the fibers. Subsequently, the swab is dipped in an aqueous extraction reagent containing a mixture of enzymes produced by the bacterium *Streptomyces albus* and which effect release of Streptococcus A antigen from the swab. An indicator reagent is provided that contains antibody that is specifically reactive with the Streptococcus A antigen. When the extraction reagent containing Streptococcus A antigen (if Streptococcus A antigen is present in the biological sample) is added to the indicator reagent, a detectable antibody-antigen reaction occurs.

An important feature of the invention is the use of the extraction reagent containing enzymes that effect release of Streptococcus A antigen from a swab. It has been found that merely swabbing an infected area with a swab and placing the swab in a non-enzyme containing solution does not provide reliable results. It is believed that the Streptococcus A antigen tends to cling to the fibers of the swab rather than dissolving freely into an aqueous medium which does not contain enzymes. It is found, however, that in the presence of an enzyme mixture obtained from *Streptomyces albus*, Streptococcus A antigen is released into an aqueous medium. The mechanism of antigen release is unknown; however, it is believed that the enzymes release that portion of the Streptococcus A antigen molecule containing the antibody-reactive determinant(s) from that portion of the molecule that tends to cling to the swab fibers.

Extraction reagent containing *Streptomyces albus* enzymes is prepared as follows:

*Streptomyces albus* (NCTC #7807) is grown at 25° C. for 5 days in Mycophil (Trademark) agar obtained from the BBL Microbiology Division of Becton, Dickinson and Commpany, Cockeysville, Md. The organisms are then transferred into 40 ml of liquid medium and allowed to grow for 5 days at 25° C., with shaking. The liquid medium consists of Yeast Extract, polypeptone, dextrose, polysorbate 80 (Tween), and potassium monobasic phosphate.

After 5 days, the 40 ml of liquid medium is transferred to 400 ml of the same medium and incubated at 25° C. with shaking. Between 5 and 14 days aliquots of the culture broth are taken and evaluated for their ability to lyse Streptococcus pyogenes (ATCC #8135) cells.

The culture fluid is harvested by centrifugation at 10,000–13,000×g for 30 minutes. The supernate is then filtered through cheesecloth and dialyzed against 0.05M Tris pH 8.0. Aliquots are then lyophilized and kept at 4° C.

Furthermore, it is found that the correct choice of an applicator is an important factor affecting test reliability. Many common types of applicators used for gathering specimens do not work well in the test of the present invention. In particular, swabs formed of natural cellulosic material are found to work very poorly. In accordance with an important aspect of the invention, it is highly preferable that the culture swab be formed of regenerated cellulose (rayon) fibers. Rayon is preferred not only over cotton but over other synthetic fibers which are otherwise useful for forming culture swabs.

Another important discovery with respect to the present invention is that applicator sticks made of natural material, such as wood, are not suitable for obtaining good results. In accordance with another important aspect of the invention, it is preferred that the applicator sticks be formed of synthetic material, especially material that is non-porous, including non-porous plastics such as polystyrene, polycarbonate, polypropylene, polyethylene, polytetrafluoroethelene, polyamides and polyacrylics.

It is surprising that regenerated cellulose fiber is most effective for collecting Streptococcus A antigen whereas natural cellulosic materials, such as cotton and wood, are unsuitable. This finding indicates that the system is very sensitive to the presence of substances which are present along with cellulose in natural materials. The mechanism or mechanisms which cause this sensitivity have not been determined; however, several factors may be involved. It may be that natural cellulosic materials contain substances which inhibit the enzymes that are used to release the Streptococcus A antigen from the fibers. Another possibility is that natural cellulosic fibers contain substances which react with the antigenically active sites of the Streptococcus A antigen, rendering the antigen unrecognizable by the antibody. Porous material, such as wood, may further interfere with clear results by absorbing the antigen, enzymes or other reagents. The possible mechanisms by which natural cellulosic materials interfere with detection of Streptococcus A antigen are set forth as possible explanations for the surprisingly superior results achieved using synthetic materials; however, because the possible explanations have not been closely examined, applicants are not bound by any such possible explanations for the results.

In accordance with a preferred embodiment of the invention, presence of Streptococcus A antigen in the extraction reagent is detected by an agglutination indicator reagent that contains suspended latex particles to which the antigen-reactive antibody is bound. Binding of antigen molecules by antibodies bound to different latex particles results in crosslinking of the latex particles, causing them to agglutinate and precipitate out of suspension. Agglutination can be detected with the naked eye, but preferably is noted by examination with a microscope.

Suitable latex particles may be purchased from Polysciences, Inc., Warrington, Pa. in carboxylated form. The particles range in size from about 0.2 to about 1.0 microns and typically have between about $1 \times 10^{10}$ and about $1 \times 10^{12}$ antibody molecules per $cm^2$ of particle surface area. The indicator reagent has from between about $1 \times 10^{-3}$ and about $10 \times 10^{-3}$ gm of antibody-bound latex particles per ml. The antibody for preparing the particles are preferably obtained by immunizing rabbits with Strain T-23 Group A beta-hemolytic streptococci. Active antibody is recovered from the serum of these rabbits by a combination of precipitation in the presence of 50% saturated $(NH_4)_2SO_4$ and ion exchange chromatography using DEAE-cellulose (DE-52, Whatman) equilibrated with Tris buffer, 0.01M pH 8.0. The active antibody fraction is eluted from the DEAE cellulose column by the use of a NaCl gradient. The active antibody fractions elute from the column at between 0.04 and 0.09M NaCl.

Latex-antibody reagent is prepared by coupling rabbit anti-Group A Streptococcus antibody to carboxylated latex using 1-ethyl-3-(3-dimethyl aminopropyl) carbodiimide (EDC) as the condensing agent.

It should be understood that the invention is not limited to detection of Streptococcus A through agglutination of antibody-bound latex particles, and numerous other suitable methods of detecting antibody-antigen reactions could be substituted, including but not limited to radioimmunoassay and immunofluorescent techniques. An advantage of the immunoagglutination technique is that it is simple to perform, gives results within minutes and is clearly readable.

A test kit according to the invention provides suitable applicators with plastic sticks and rayon swabs. Enzyme-containing extraction reagent is typically provided in lyophilized form for on-site reconstitution. After reconstitution, the extraction reagent may be stored refrigerated (about 2° C. to about 8° C.) for about 10 days. The indicator reagent is provided as a stable suspension and can be stored refrigerated for about 12 months. The suspension is shaken prior to use. A test kit also preferably provides additional supplies for performing the test to insure that the most suitable supplies are used and to prevent the use of materials which might interfere with the test. Such supplies can include test tubes of appropriate size in which antigen is extracted from the swabs, multi-well test plates for performance of the agglutination reaction, hand stirring sticks, transfer pipette tips, etc. A test kit should also provide positive (Streptococcus A antigen-containing) and negative control samples. It is also preferred that as a further control, the test kit includes a latex suspension that contains no antibodies for direct comparison (bearing in mind that even a non-agglutinated suspension appears somewhat cloudy).

Reconstituted extraction reagent is pipetted into clean test tubes (typically about 0.5 ml per tube). The applicators are used to swab infected areas, e.g., throats, and then the swab end of each stick is placed in one of the tubes. The tubes are incubated for at least 30 minutes and preferably an hour at about body temperature (37 C.) to allow the enzyme to release the Streptococcus A from the fiber. During incubation, it is preferred that the top of the test tube be covered by any suitable means to prevent evaporation. After the incubation period, the applicator swab is pressed against the sides of the tube to release its liquid as the applicator is withdrawn. The applicator is then discarded. An aliquot, e.g., 50 ul, of each sample is placed in each of two wells of a sample plate, as are aliquots of positive and negative controls to provide three sets of paired wells. To one of the paired wells is added antibody-containing latex suspension and to the other of the two wells is added antibody-free latex suspension. Using individual plastic stirring sticks, the reagents in each well are mixed. The sample plate is covered and placed on a mechanical rotator for about 4 minutes. The results are immediately readable. Although a strong agglutination reaction is visable to the naked eye, it is preferred that the mixtures in the wells be observed under a microscope. Any difference observed in the antibody-containing latex suspension well from the antibody-free latex suspension well indicates the presence of Streptococcus A in the swabbed area. If there is no difference in the two wells, it can be concluded that Streptococcus A is not present.

EXAMPLE 1

4.0 ml of carboxylated latex having 2.5 weight percent solids, obtained from Polysciences, Inc., Warrington, PA, is washed three times with distilled water. After the final wash the particles are resuspended in 4.0 ml of distilled water. One ml of 0.05M $KH_2PO_4$, pH 4.5 is added. The suspension of latex is placed in a magnetic stirrer and maintained at 22° C. 5.0 ml of a solution of 2 weight percent EDC (obtained from Sigma Chemical Company, St. Louis, MO) is added and allowed to react for 3.5 hrs. The carbodiimide latex is washed once in saline (0.9% NaCl) and resuspended in 5.0 ml of saline (0.9% NaCl).

1.2 mg of rabbit antibody is dissolved in 5.0 ml of 0.2M borate, pH 8.5, and the 5.0 ml of activated latex suspension in saline is added. The latex and rabbit antibody are allowed to react for 20 hrs. at 22° C. To neutralize surface carboxyl groups not bound to the antibody, a solution of 5 mM ethanolamine is added, followed by a solution of bovine serum albumin at a concentration of 2 weight percent. The antibody-latex is washed and taken up in 0.1M glycine pH 8.2 containing 0.9% NaCl, 0.2% $NaN_3$, 0.2% BSA, and 0.05% Tween-20, and is stored at 4° C.

EXAMPLE 2

The performance of the Group A Streptococcus latex agglutination test described above was determined in a multi-center clinical evaluation. The latex agglutination test results were compared to culture results.

Pharyngeal swabs were collected from 1440 adults and children who exhibited the symptons of pharyngitis. Specimens were collected on a rayon swab and transported to the laboratory in Modified Stuart's Medium (Marion Culturette). Prior to the performance of the assay of the invention, each swab was used to inoculate a sheep blood agar plate for culture. After 18-24 hours of incubation, beta-hemolytic colonies were grouped by the capillary precipitin test. The latex agglutination test method of the invention agreed with the culture results in 95% (1366/1440) of the swab specimens. The results are summarized in Table 1.

TABLE 1

| AGREEMENT BETWEEN THE AGGLUTINATION TEST AND CULTURE RESULTS | | |
|---|---|---|
| Culture Results | Agglutination Positive | Agglutination Negative |
| Positive for Group - 309 A Streptococcus | 281 | 28 |

TABLE 1-continued

| AGREEMENT BETWEEN THE AGGLUTINATION TEST AND CULTURE RESULTS | | |
|---|---|---|
| Culture Results | Agglutination Positive | Agglutination Negative |
| Negative for Group - 1131 A Streptococcus | 46 | 1085 |

EXAMPLE 3

The sensitivity of the Group A Streptococcus latex agglutination test was determined from 309 pharyngeal swab specimens which were determined to be positive by culture for beta-hemolytic streptococci and confirmed as Group A by the capillary precipitin test. Two hundred eighty-one (281) of these specimens (91%) were positive by the latex agglutination test of the invention. The sensitivity of the test was 95% if those swabs which grew out less than 10 colonies of Group A Streptococcus on culture were ignored.

EXAMPLE 4 the specificity of the Group A Streptococcus latex agglutination test was determined from 1067 pharyngeal swabs yielding cultures negative for beta-hemolytic streptococci and from 64 pharyngeal swabs yielding cultures which grew a beta-hemolytic streptococcus confirmed by the capillary precipitin test as being other than Group A. Of these, 1085 samples were agglutination negative, yielding a specificity of 96%.

Although the invention has been described in terms of certain preferred embodiments, modifications obvious to one with ordinary skill in the art may be made without departing from the scope of the invention.

Various features are set forth in the following claims.

What is claimed is:

1. A test kit for the detection of Streptococcus A comprising
   applicator means for collecting a biological sample potentially containing Streptococcus A, said applicator means including an applicator stick and a swab at one end formed of a fiber that collects Streptococcus A antigen,
   a container comprising an extraction reagent containing enzymes produced by *S. albus* for releasing Streptococcus A antigen from said swab and
   a container comprising indicator reagent containing antibody reactive with Streptococcus A antigen,
   whereby when a biological sample is collected with said fiber swab of said applicator means, said swab is placed in said extraction reagent for a time sufficient to release Streptococcus A antigen into said extraction reagent, and an aliquot of said extraction reagent is mixed with said indicator reagent, the presence of Streptococcus A in said biological sample is indicated by the occurrence or nonoccurrence of an antibody-antigen reaction.

2. A test kit according to claim 1 wherein said swab is formed of regenerated cellulose fiber.

3. A test kit according to claim 1 wherein said stick is formed of synthetic material.

4. A test kit according to claim 1 wherein said stick is formed of non-porous material.

5. A test kit according to claim 1 wherein said swab is formed of regenerated cellulose fiber and said stick is formed of plastic.

6. A test kit according to claim 1 wherein said indicator reagent contains antibody bound to suspended latex particles which agglutinate when said antibody binds to said antigen, occurrence or nonoccurrence of an antibody-antigen reaction being observed by agglutination or non-agglutination of said suspended particles.

7. A method for detecting Streptococcus A comprising providing an applicator including an applicator stick with a fibrous swab and swabbing a biological sample with said swab, providing an extraction reagent containing enzymes produced by *S. albus* for effecting release of Streptococcus A antigen from said swab, dipping said swab in said extraction reagent and incubating said swab within said extraction reagent for a period of time sufficient to release antigen from said fibrous swab, providing indicator reagent containing antibody reactive with said antigen and adding an aliquot of said extraction reagent thereto, and noting the occurrence or nonoccurrence of an antibody-antigen reaction, indicating the presence or absence of Streptococcus A in said biological sample.

8. A method according to claim 7 wherein said swab is formed of regenerated cellulose fiber.

9. A method according to claim 7 wherein said stick is formed of a synthetic material.

10. A method according to claim 7 wherein said stick is formed of non-porous material.

11. A method according to claim 7 wherein said swab is formed of regenerated cellulose fiber and said stick is formed of plastic.

12. A method according to claim 7 wherein said indicator reagent contains antibody bound to suspended latex particles which agglutinate when said antibody binds to said antigen, occurrence or nonoccurrence of an antibody-antigen reaction being observed by agglutination or non-agglutination of said suspended particles.

* * * * *